United States Patent [19]

Jensen et al.

[11] Patent Number: 4,673,401
[45] Date of Patent: Jun. 16, 1987

[54] MALE INCONTINENCE DEVICE

[76] Inventors: Ole R. Jensen, 646 Orangeburg Rd., River Vale, N.J. 07675; Keith T. Ferguson, 231 Katherine St., Scotch Plains, N.J. 07076

[21] Appl. No.: 595,827

[22] Filed: Apr. 2, 1984

[51] Int. Cl.⁴ .............................................. A61F 5/44
[52] U.S. Cl. ................................................... 604/353
[58] Field of Search ............................. 604/338–345, 604/323, 327, 335, 347, 349, 350, 353

[56] References Cited

U.S. PATENT DOCUMENTS

| | | |
|---|---|---|
| 3,357,430 | 12/1967 | Rosenberg ............................ 604/353 |
| 4,421,509 | 12/1983 | Schneider et al. .................... 604/327 |
| 4,460,363 | 7/1984 | Steer et al. ............................ 604/342 |
| 4,553,968 | 11/1985 | Komis ................................... 604/349 |
| 4,568,340 | 2/1986 | Giacalone ............................. 604/353 |

FOREIGN PATENT DOCUMENTS

| | | |
|---|---|---|
| 674158 | 4/1939 | Fed. Rep. of Germany ...... 604/349 |
| 8000535 | 4/1980 | PCT Int'l Appl. .................. 604/349 |
| 863295 | 3/1961 | United Kingdom ................ 604/349 |

Primary Examiner—C. Fred Rosenbaum
Assistant Examiner—J. L. Kruter
Attorney, Agent, or Firm—James & Franklin

[57] ABSTRACT

A urine collection receptacle is detachably mounted to a brief. The weight of the receptacle is supported by the brief. The wall of the brief has an opening defined by aligned, oppositely facing rigid annular parts. The receptacle has a penis receiving opening defined by a rigid annular part which releasably engages the annular part on the exterior wall of the brief. A flexible membrane engages the penis to prevent urine back-up into the brief. The membrane may attach directly to the annular part on the interior wall of the brief or may be mounted on an annular part which releasably engages the annular part on the interior wall of the brief. The diameter of the annular parts is larger than that of the penis to enable the penis to be freely received through the parts and into the receptacle.

21 Claims, 9 Drawing Figures

MALE INCONTINENCE DEVICE

The present invention relates to incontinence devices and, more particularly, to an incontinence device designed for use by males which consists of a brief and a detachable urine receptacle within which the penis is freely received in a comfortable manner and wherein the brief supports virtually the entire weight of the urine receptacle.

Incontinence is the loss of body function control and, particularly, the inability to control the excretion of waste products from the body. Urinary incontinence is the loss of bladder control. The inability to control the bladder is a common problem and may result from a variety of physical or mental dysfunctions.

Since the problem of incontinence may be temporarily or permanently incurable, a variety of different devices have been devised to eliminate the embarrassment and social stigma associated with the loss of bladder control, and permit incontinence sufferers to lead relatively normal lives. For example, undergarments in the forms of briefs or the like having specially designed internal pockets to receive disposable absorbent pads have been used. The absorbent pads function to absorb urine as it is released. However, such pants and pads are most useful for females with urinary incontinence. Specially designed diapers have been utilized for bowel control problems. This approach is sometimes adequate, but may be psychologically detrimental because adults often find the use of such diapers demeaning.

For men with urinary incontinence, devices designed to externally engage the penis have been used. Such devices normally includes an external catheter in the form of a tight-fitting condom-type member. The member, at the normally closed end, is provided with a plastic connector. The connector is fastened to a discharge tube which, is turn, is connected to a urine collection receptacle such as a bottle or bed pan. This approach is commonly used with non-ambulatory men.

In order to make the external catheter collection device mobile, the urine collection receptacle may take the form of a plastic bag or the like, designed to be strapped to the calf of the patient. The discharge tube is caused to extend from the condom down the inside leg of the patient's pants to the bag. However, present systems of this type suffer from several disadvantages which make them uncomfortable to wear, irritating, and, under certain circumstances, incapable of containing the urine discharge.

One of the major problems associated with external catheter incontinence devices relates to the fact that the penis must be tightly engaged by the condom-like member to prevent the condom from slipping off the penis. This, at best, leads to an uncomfortable situation and may, in the extreme case, result in irritation or injury to the penis.

In addition, movement of the patient or the bag may cause a significant force to be applied to the condom and, thus, the penis. Normally, the length of the discharge tube is such that the weight of the bag is supported by the leg and only a small amount of force (equal to the weight of the tube) is exerted on the condom. However, under certain circumstances, such as if the bag slips partially down the leg or the patient stretches, the discharge tube may prove to be too short to accommodate the situation. This often results in the exertion of sufficient force on the condom to pull the penis and even remove the condom from the penis.

In order to prevent removal of the condom from the penis, various methods of mounting the condom on the penis have been devised. Elastic and non-elastic strips have been wound around the condom and the penis. Adhesive elements have been used between the condom and the penis. Wrapping a band around the penis to hold the condom securely thereto is uncomfortable and, in the extreme case, can cause sores, rashes, or even gangrene. The use of an adhesive to retain the condom on the penis is also uncomfortable and, in many cases, ineffective because the adhesive will release if it becomes saturated, thereby permitting the urine to leak out of the top of the condom.

Another major problem with conventional external collection devices is that when the patient sits down, the discharge tube may "kink," preventing the free passage of liquid therethrough. This results in a urine back-up, causing the penis to become irritated and eventually the leakage of urine from the top of the condom.

The collection bag is normally strapped to the calf of the patient by one or more belts which surround the calf. This is uncomfortable because the leg must bear the weight of the bag and urine. In addition, as the bag fills up and the weight increase, the bag tends to sag or move downwardly along the calf, increasing the tension on the discharge tube.

Attempts have been made to alleviate some of the above-mentioned problems by permanently affixing a condom-like member to a diaper. However, in such devices, the condom-like member must still adhere tightly to the penis. Since the condom-like member has insufficient structural rigidity to support the weight of the collection receptacle, the penis must support the weight and, thus, tends to be pulled downwardly by the weight of the bag, leading to discomfort. Moreover, such devices are difficult to put on and "kinking" of the discharge tube still may cause urine back-up.

In general, the present invention eliminates the above-mentioned problems by eliminating the necessity for a tight fitting penis engaging member and, in the preferred embodiment, the necessity for a dishcarge tube leading to the urine collection receptacle. The penis is freely received within the urine collection receptacle and is not subjected to any substantial force such as the force developed due to the weight of the receptacle. In the preferred embodiment, the urine receptacle takes the form of an elongated flexible bag which is detachably mounted to a brief to support same and anchored to the leg for stability. The receptacle is preferably designed for anchoring to the thigh, but may be made long enough to be anchored below the knee, if desired. Virtually the entire weight of the urine collection receptacle is supported by the brief. The large internal diameter of the urine collection receptacle insures a free flow of urine. The use of a non-return flow valve in the bag and a detachable flexible membrane acting as a gasket to prevent urine back-up.

By detachably mounting the receptacle and the gasket to the brief, the brief can be separated from the receptacle and gasket such that it is washable and reusable. Further, the same brief can be used with different embodiments of the receptacle and with gaskets having different mounting structures.

This invention provides a male incontinence device in which patient comfort is enhanced by eliminating the exertion of force on the penis. Patient comfort is enhanced because the penis is not squeezed or tightly encircled by a condom-like member and the weight of the collection receptacle is supported by a brief and not the penis or leg of the patient.

The present invention provides a male incontinence device which is easy to put on and remove because of a multi-part structure which includes a brief which can be washed and reused and a collection receptacle detachably mounted to the brief.

The present invention provides a male incontinence device comprising a brief which can be used with receptacles of different structures.

The present invention provides a male incontinence device which prevents urine back-up by eliminating "kinking" of the discharge tube.

The present invention provides a male incontinence device which enables the collection receptacle to be mounted in a manner which minimizes spilling of collected fluids.

In accordance with the present invention, a male incontinence device is provided comprising an undergarment in the form of a brief and a flexible liquid collection receptacle. Means are provided for releasably mounting the receptacle to the brief. The mounting means comprises first and second substantially rigid annular parts affixed to the brief and receptacle, respectively. Means are provided for releasably interengaging the parts in a load bearing manner to support the weight of the receptacle. The brief comprises an opening adapted to be aligned with the penis. The brief opening is defined by the first rigid annular part, which is affixed to the brief.

A flexible membrane situated proximate the brief opening is provided. The membrane has an expandable opening adapted to lightly sealingly engage the penis. Preferably, means are provided for mounting the membrane to the brief. In one embodiment, these means comprise a third substantially rigid annular part affixed to the brief, in alignment with the first part, but mounted on the surface of the brief opposite the first part. The first and third parts may be integral.

The membrane may be mounted on a fourth annular part which has means for releasably interengaging the third part. Alternatively, the membrane may have a ring-like portion adapted to engage the third part.

The first part has an outwardly extending flange. Means are provided to affix the flange to the brief. The third part also has an outwardly extending flange. The flanges are spaced from each other and define a recess into which a portion of the brief is received. The receptacle comprises a hollow flexible member having an opening therein defined by the second substantially rigid annular part. The annular parts have internal diameters substantially larger than the diameter of the penis such that the penis is freely received therethrough in a non-load bearing manner.

In one preferred embodiment, the member is elongated and means are provided mounted proximate the lower end of the member for anchoring the member to the leg. A non-return liquid flow valve is situated in the interior of the member below the second part to prevent urine back-up.

In a second preferred embodiment, the receptacle includes a condom-like member connected to a collection bag by means of a corrugated conduit. The bag is adapted to be mounted on the lower leg.

The interengaging means comprises an annular groove or channel on one of the annular parts in each mating pair and an annular protrusion on the other of the mating parts. The groove and protrusion interengage in a snap-fit manner. The first and second parts interengage with sufficient strength to support the weight of the receptacle. The brief acts to distribute the weight of the receptacle over a large area and, particularly, along the waistband of the brief. Thus, the weight of the receptacle need not be supported by the penis.

To these and to such other objects which may hereinafter appear, the present invention relates to a male incontinence device, as described in the following specification and recited in the annexed claims, taken together with the accompanying drawings, wherein like numerals refer to like parts, and in which:

Figure 1:
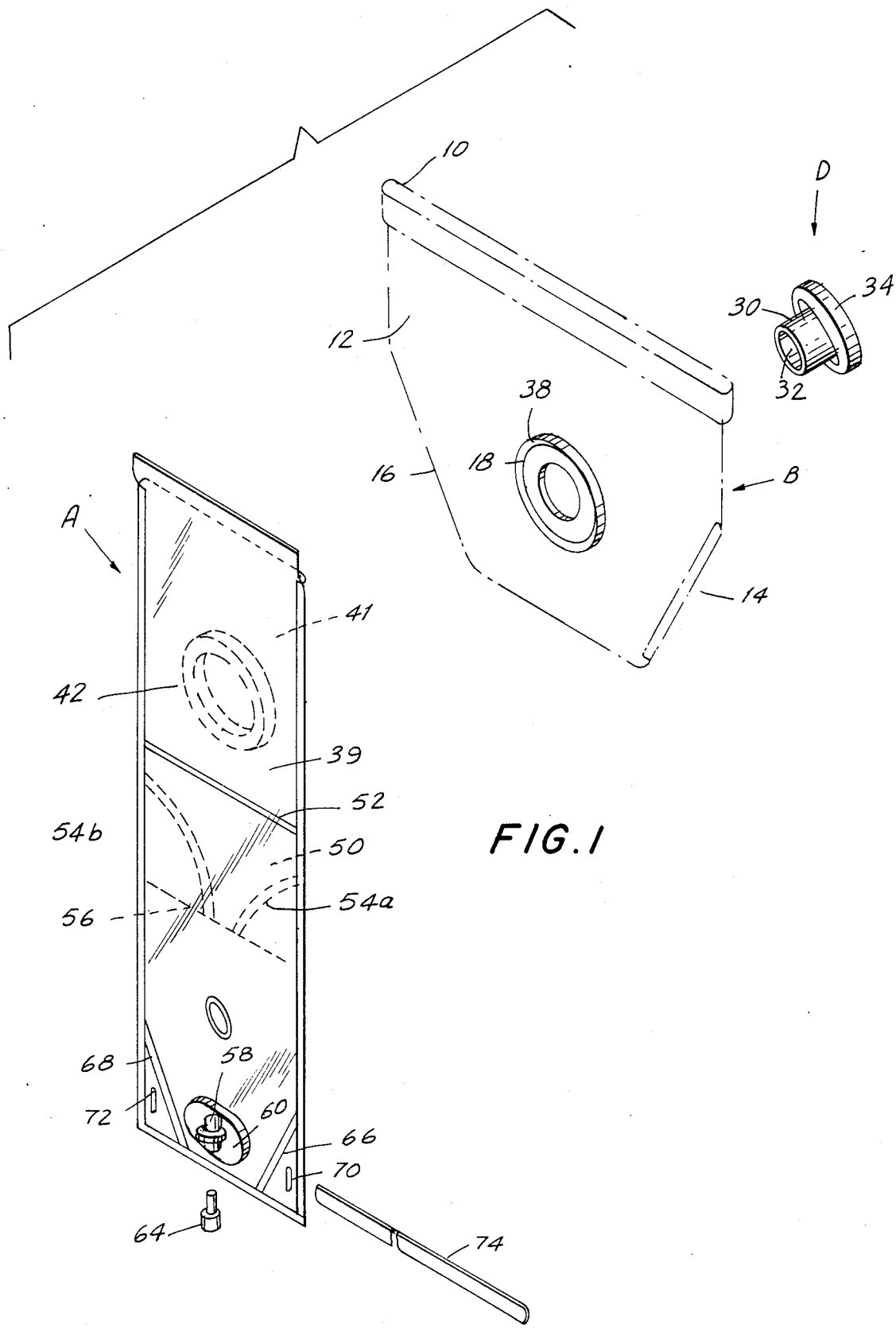
FIG. 1 is an exploded isometric view of the male incontinence device of the present invention illustrating the first preferred embodiment of the receptacle.
Figure 2:
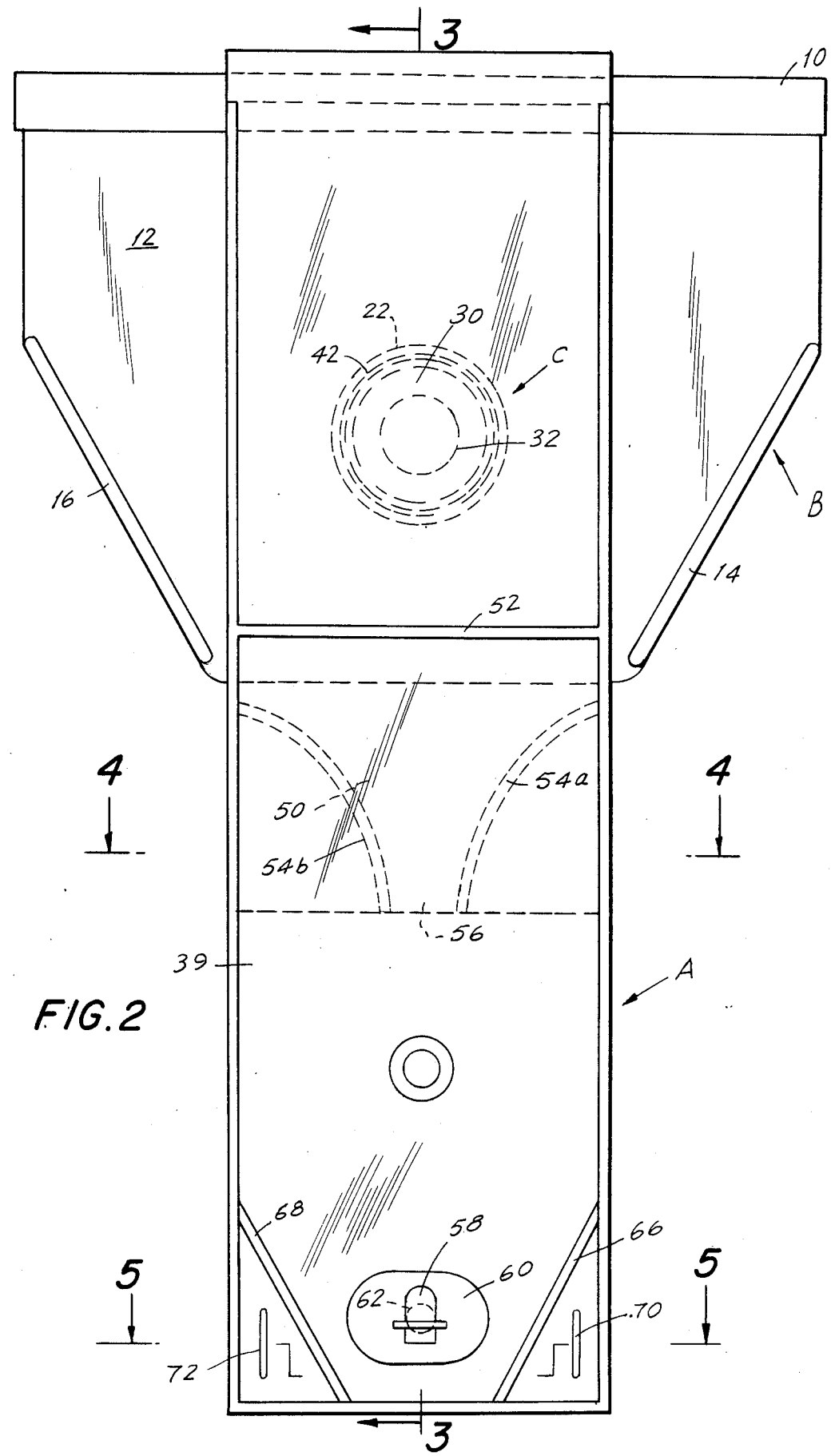
FIG. 2 is a front plan view of the version of the male incontinence device of the present invention shown in FIG. 1.

As illustrated in the drawings, the male incontinence device of the present invention includes a urine collection receptacle, generally designated A, which is adapted to be detachably mounted to a brief, generally designated B, and anchored to the leg of the patient. Brief B preferably takes the form of a conventional, relatively tight fitting undergarment which is modified to accommodate receptacle A. Brief B has an elastic waistband 10, or an adjustable waistband (not shown) such that brief B, and particularly the waistband thereof, fits the wearer snuggly. As will become apparent, this feature is important becuase the weight of the receptacle is supported by the brief and, thus, the brief must fit without sagging or falling down. Brief B also includes a body portion with a front wall 12 made of soft fabric such as cotton or the like, and leg openings 14 and 16, similar to conventional garments of this type.

The front wall 12 of brief B is provided with a circular opening adapted to align with the penis when brief B is properly situated on the wearer. The opening is defined by receptacle mounting means. The opening is defined by receptacle mounting means, generally designated C. Means C preferably comprises a pair of oppositely oriented substantially rigid annular parts 18 and 20, which may be integral or non-integral as desicribed below. Parts 18 and 20 are made of any suitable plastic material, such as polyethylene, PVC, or the like, such that brief B can be washed without adversely affecting the parts.

Figure 3:
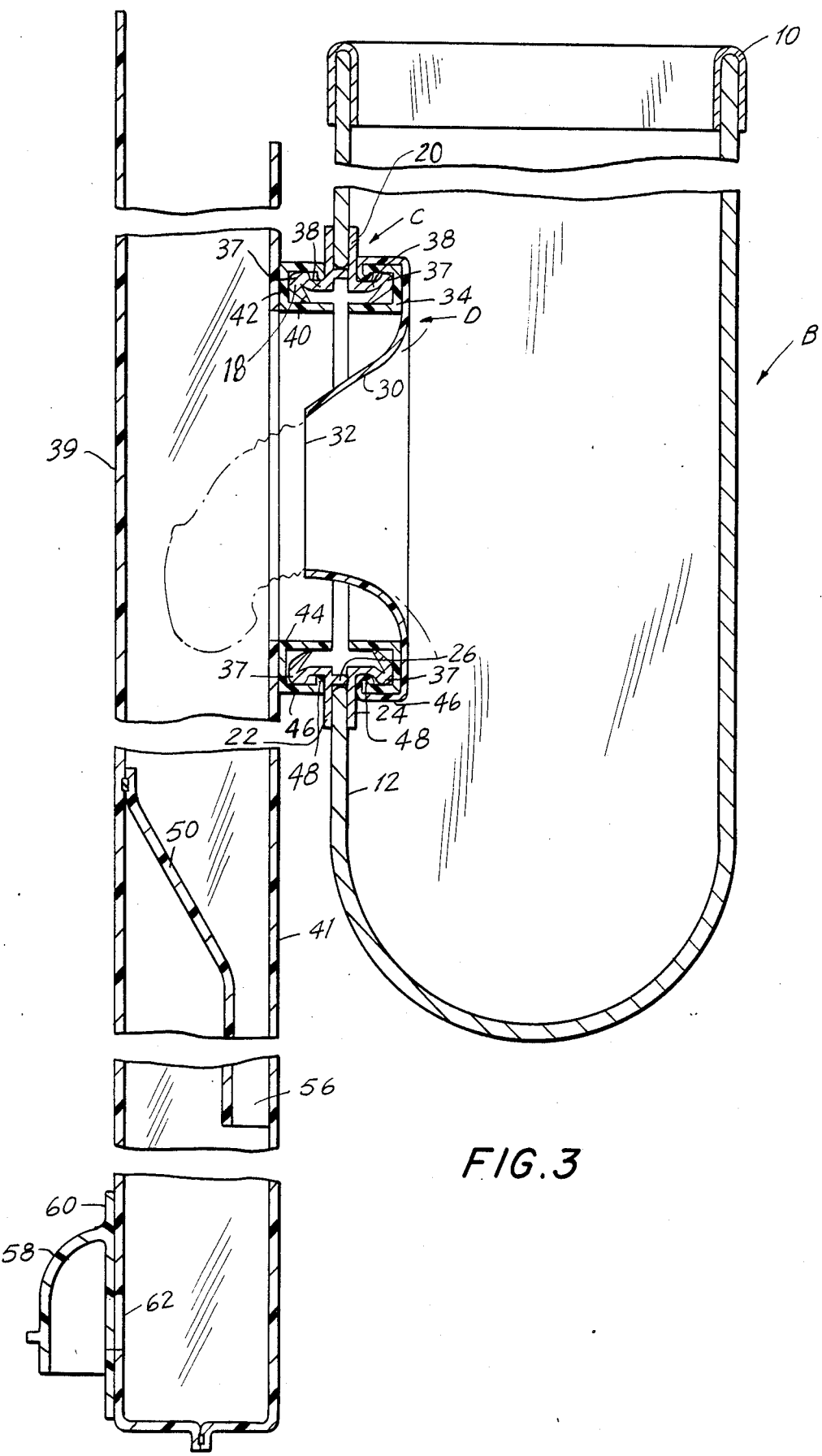
FIG. 3 is a side cross-sectional view of the male incontinence device of the present invention taken along line 3—3 of FIG. 2, illustrating one preferred embodiment of the annular interengaging parts.
Figure 4:
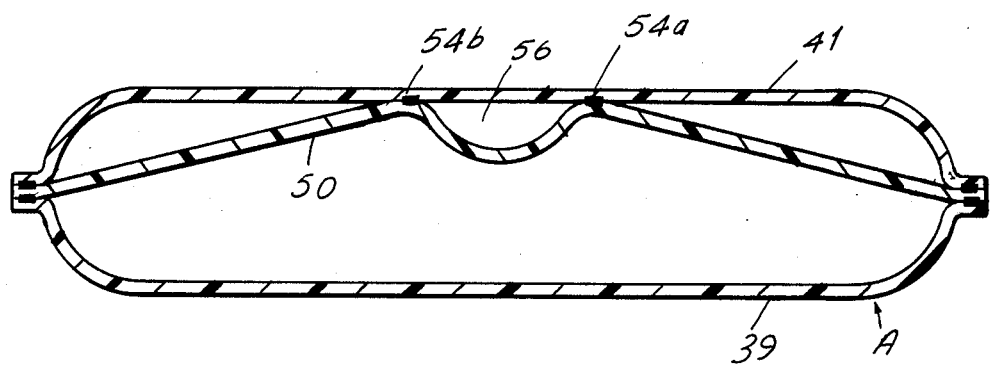
FIG. 4 is a cross-sectional view of the male incontinence device of the present invention taken along line 4—4 of FIG. 2.
Figures 6, 8:
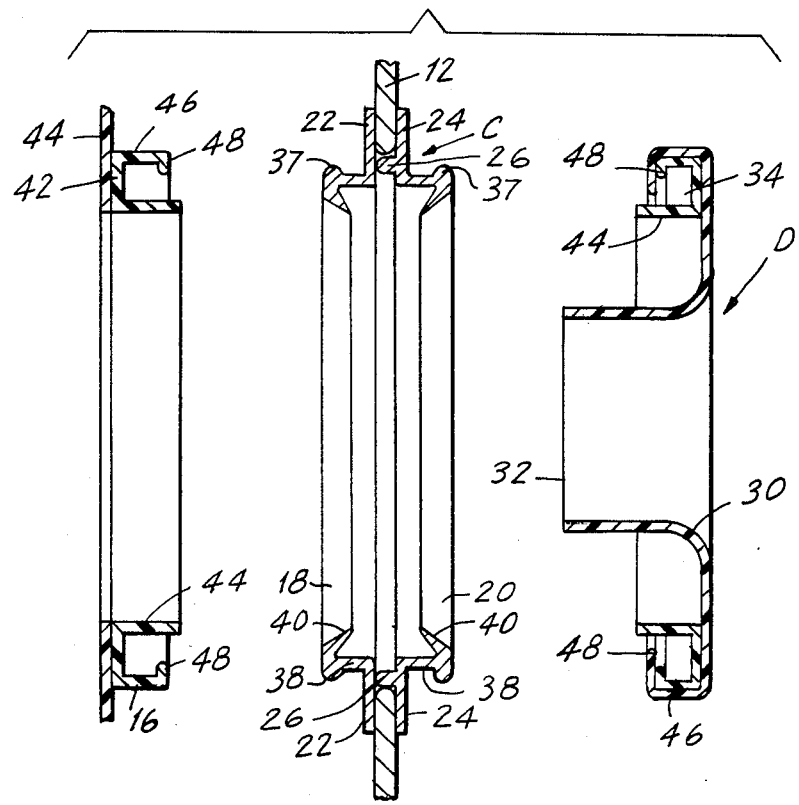
FIG. 6 is an exploded side view of the first preferred embodiment of the annular interengaging parts.
FIG. 8 is an exploded side view of the alternate preferred embodiment of the annular interengaging parts.
Figure 7:
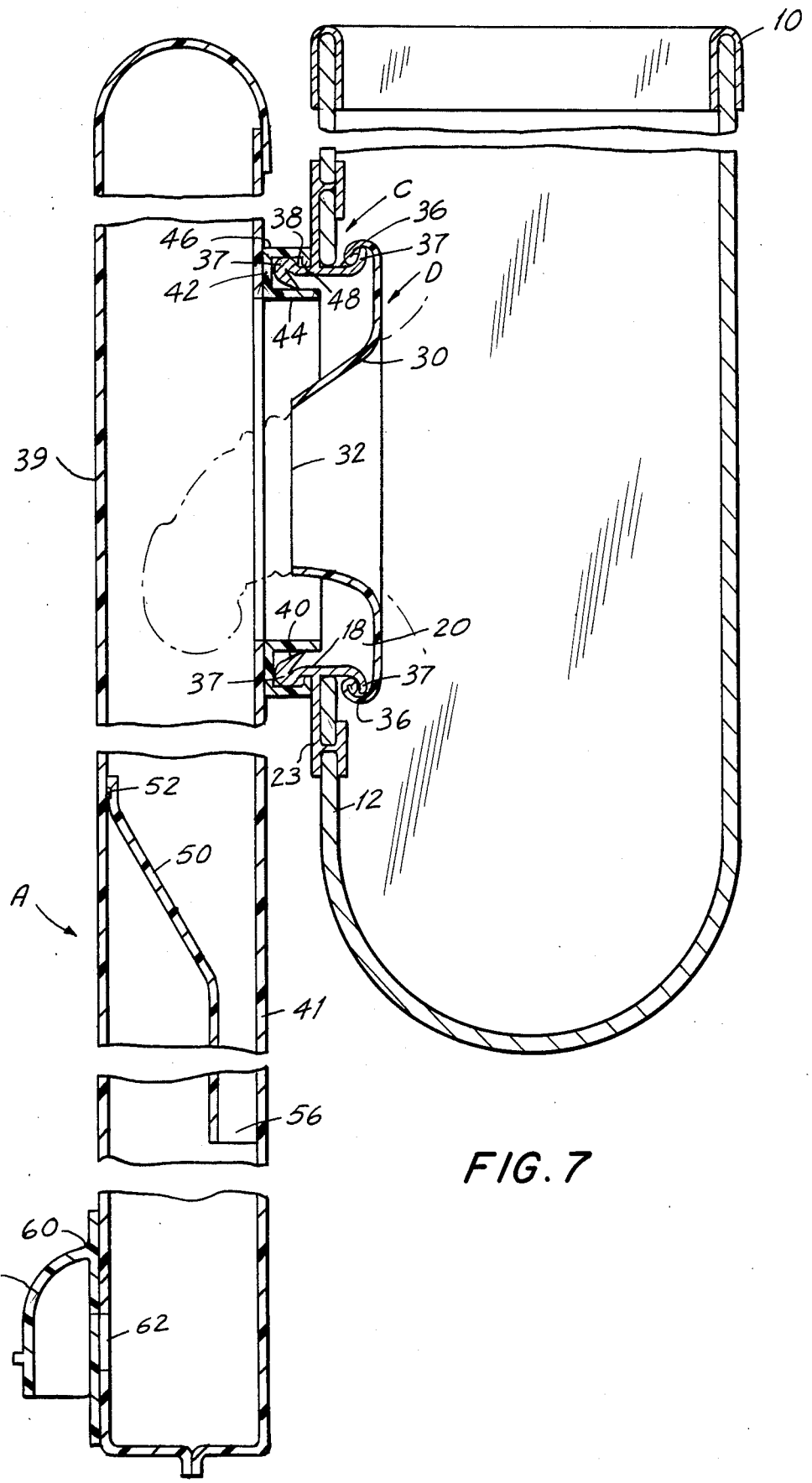
FIG. 7 is a view similar to FIG. 2, showing an alternate preferred embodiment of the annular interengaging parts and an alternate preferred embodiment of the means for mounting the membrane.

Part 18 is mounted to the exterior surface of wall 12 and part 20 is mounted to the interior surface thereof. When parts 18 and 20 are non-integral, as illustrated in FIGS. 3 and 6, each is provided with an outwardly extending flange 22, 24, respectively. When parts 18 and 20 are integral, as shown in FIGS. 7 and 8, a single flange 23 is provided. The flanges facilitate the mounting of parts 18, 20 on brief B.

When parts 18 and 20 are non-integral, one or more protrusions 26 are provided on one of the flanges 22, 24. Protrusions 26 serve to space the flanges apart to form a recess into which wall 12 of the brief may be received. Protrusions 26 also constitute ultrasonic sealing members by which the parts 18 and 20 can be joined and retained on brief B. When parts 18 and 20 are integral, flange 23 is heat sealed to wall 12 such as through the use of a heat sealing member 25 or affixed to wall 12 in any conventional manner.

Whether integral or not, parts 18 and 20 are of substantially the same size and, in particular, have substantially equal inner diameters. The inner diameters are substantially larger than the diameter of the penis such that the penis can be freely received through the parts without being engaged.

Receptacle A is provided with a similar substantially rigid annular part, described below, for releasably mounting to part 18. A gasket, generally designated D, is provided for mounting on part 20 on the interior surface of wall 12.

Gasket D is preferably a very thin flexible membrane 30 with a central opening 32 therein. Membrane 30 is preferably made of latex or the like and functions to lightly sealingly engage the penis to prevent urine back-up into the interior of brief B. The opening 32 in membrane 30 is easily expandable such that membrane 30 exerts minimal force on the penis.

Membrane 30 is preferably detachably mounted to part 20. As illustrated in FIGS. 3 and 6, membrane 30 may be mounted on a substantially rigid annular part 34 which is designed to interengage with part 20 in a snap-fit fashion. The flexibility of the membrane permits it to be easily situated around part 34 and held in place thereon. Alternately, as illustrated in FIGS. 7 and 8, membrane 30 can be provided with a ring-like edge portion 36 at the end thereof which can itself be expanded and mounted on part 20, eliminating the necessity for part 34. In this case, the outwardly extending ridge 37 on part 20 may be enlarged slightly to insure a positive attachment.

As best seen in FIGS. 3 and 6, parts 18 and 20 each comprise an annular protrusion including a cylindrical rib 38 extending in a substantially perpendicular direction with respect to the surface of brief B. A thin resilient flexible and deflectable sealing protrusion 40 extends inwardly from each rib 38 at an angle toward brief B. Protrusion 40 is of tapering form and serves to provide a positive engagement and sealing with the mating part.

In the embodiment illustrated in FIGS. 1-3 and 7, receptacle A has a generally elongated rectangular shape and is composed of any flexible water-proof plastic material, preferably transparent or opaque. Receptacle A has a front wall 39 and a rear wall 41 which are heat sealed along the edges and bottom in order to form a hollow urine receptacle or bag. The top of the receptacle may be open, as shown in FIGS. 1 and 3, or folded over and sealed to rear wall 41, as illustrated in FIG. 7.

Near the top of rear wall 41 is an opening defined by a second substantially rigid annular part 42 which is heat sealed or otherwise affixed to rear wall 41. The inner diameter of part 42 is substantially equal to the inner diameter of parts 18 and 20 and, thus, is substantially larger than the diameter of the penis.

Part 42 has a structure similar to that of part 34. Both include an annular channel or groove which forms a female-type structure designed to engage the cylindrical rib 38 of male parts 18 and 20, respectively, in a "snap-fit" fashion. Parts 42 and 34 are defined by outwardly extending spaced walls 44 and 46. At the edge of wall 46 is provided a rim 48 which extends inwardly toward wall 44. Rim 48 and wall 44 define a restricted annular mouth or entry into the part within which rib 38 is received, as illustrated in FIGS. 3, 6, 7, and 8. Ridge 37, extending outwardly from rib 38 of parts 18 and 20, cooperates with rim 48 to provide added mechanical security. Rib 38 is dimensioned to be gripped between walls 44 and 46 to securely mount the receptacle on brief B in a load bearing fashion.

The releasable connection between parts 18 and 42 has sufficient strength to support the entire weight of receptacle A, even when same is filled to capacity. Accordingly, virtually the entire weight of the receptacle is carried by brief B. The weight of the receptacle is distributed along the wall 12 of brief B and to the waistband 10 of brief B.

Below part 42, in the interior of receptacle A, is situated a non-return valve to prevent liquid back-up from the bottom of the receptacle. The valve used in the present invention may be any conventional non-return valve, such as one, which consists of two tapering parts, each extending from a different internal surface of the wall of the receptacle. The parts are heat sealed along the edges with the bottom left open to form a funnel-like member. Liquid can flow downwardly along the funnel-like member and out the bottom opening, but is prevented from re-entering the member from the receptacle.

It is preferable, however, to employ a single piece non-return valve, of the type disclosed in European Patent Application No. 106,587 published Apr. 24, 1984 in the name of Ole R. Jensen. This type valve, as illustrated in the drawings, includes a rectangular flexible baffle 50 made of the same material as the receptacle walls. The top of baffle 50 is heat sealed to the inner surface of front wall 39 along a line 52 which extends across the receptacle from the left side to the right side. The lower portion of baffle 50 is affixed to the inner surface of wall 41 by spaced heat seals 54a and 54b, which are concavely shaped. The non-attached body portion of baffle 50 defines, in conjunction with the interior surface of wall 41, a funnel-like structure with an opened lower end 56.

The non-return valve is situated in the middle section of receptacle A, below part 42. Urine collects in receptacle A below the valve and between baffle 50 and the interior surface of wall 39 below line 52. Thus, a fairly large liquid reservoir is provided. For certain patients, a smaller capacity receptacle may be used due to limited urine excretion.

Near the lower portion of receptacle A is a drain valve member 58. Member 58 is a hollow plastic chamber situated on a flange 60 which, in turn, is affixed to the exterior surface of wall 39 by any conventional method such as heat sealing, adhesive, or the like. The hollow interior of member 58 communicates with the interior of receptacle A through an aperture 62. Member 58 is designed to receive a plug 64 which acts as a stopper to prevent liquid from flowing from the receptacle. When the bag is to be emptied, plug 64 is removed and the urine within receptacle A flows through aperture 62 and member 58 such that it can be collected and disposed of.

Figure 5:
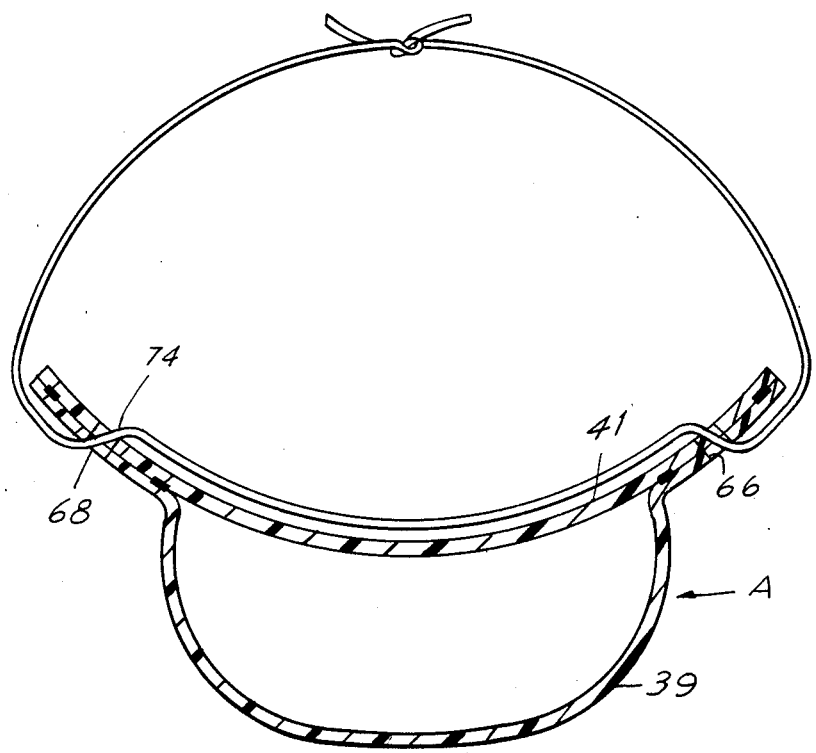
FIG. 5 is a cross-sectional view of the male incontinence device of the present invention taken along line 5—5 of FIG. 2.

The lower end of receptacle A is tapered inwardly by heat seal seams 66, 68 such that triangular portions at either corner of the bag are isolated from the interior. The triangular portions are provided with slits 70, 72 through which a band 74 is adapted to be inserted. Band 74, which is preferably made of elastic material, is designed to encircle the leg of the wearer, as illustrated in FIG. 5, so as to anchor the lower end of the receptacle to the leg to prevent same from swaying back and forth as the patient moves. The ends of band 66 may be tied or otherwise joined in any convenient manner.

In use, the patient puts on brief B as he would a conventional undergarment. Membrane 30 is mounted on part 34 either by placing ring-like portion 36 over part 20 or by snap-fitting part 34 to part 20. The penis is then extended through membrane 30 which lightly sealingly engages the exterior of the penis. Thereafter, receptacle A is aligned with the brief such that part 42 aligns with part 18 and the penis extends through the opening in rear wall 40 of receptacle A, defined by part 42. Parts 42 and 28 are then snap-fitted together such that the receptacle is mounted on brief B.

The length of receptacle A determines the point on the leg at which the lower end thereof will be anchored. It is preferable to anchor the lower end of the receptacle to the thigh. However, by increasing the length of the receptacle, same can be anchored below the knee, if desired.

Figure 9:
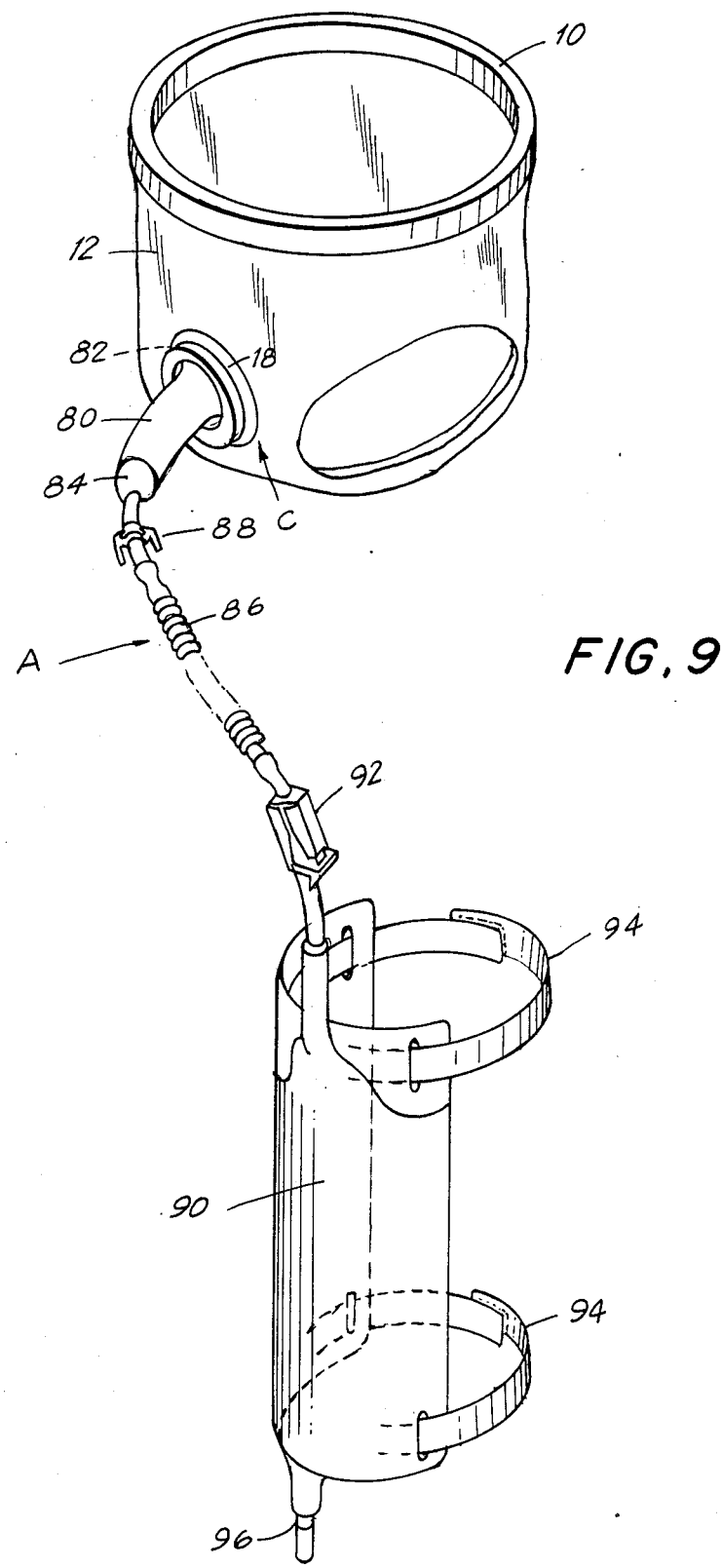
FIG. 9 illustrates an alternate preferred embodiment of the receptacle.

Receptacle A is primarily designed for use by ambulatory patients. However, for non-ambulatory patients, such as paraplegics or for night use, a second preferred embodiment, generally designated A', as illustrated in FIG. 9, may be used. Receptacle A' attaches to brief B in the same manner as receptacle A.

Receptacle A' consists of a flexible condom-shaped member 80 composed of latex or the like, mounted on a substantially rigid annular part 82. Part 82 has the same structure as part 42 of receptacle A and performs the same function, that is, to interengage with part 18 on brief B in a "snap-fit" fashion. The penis is loosely received through part 82 and within member 80 which has an internal diameter approximately equal to the internal diameter of part 82, and thus larger than the diameter of the penis.

At the end of member 80 is a connector 84 which forms an outlet port. Connector 84 is connected to a flexible corrugated conduit 86 by means of a coupling 88. Coupling 88 may be of any conventional design.

The other end of conduit 86 is connected to the inlet port of a flexible bag 90. Bag 90 may have a structure similar to that of the bag illustrated in FIGS. 1–3, except for the elimination of the opening defined by part 42 and the non-return valve. Preferably, a clamp or other type valve means 92 is provided along the conduit to provide a positive flow restriction. A valved outlet port 96 may also be provided. Bag 90 may be provided with straps 94 for mounting to the leg.

Receptable A' has the same advantages as receptacle A in that the penis is loosely received therein an all the weight of the receptacle is supported by the brief. Moreover, the corrugated flexible conduit substantially eliminates the problem of kinking.

It may be desirable to design brief B such that the opening through which the penis extends can accommodate individuals of different physical characteristics. This can be accomplished in a number of different ways. One way would be to alter the structrue of part 20 to make same elongated or oval. Membrane 30 could then be constructed such that the opening 32 thereon is offset relative to the center line. In this way, membrane 30 could be mounted on part 20 in a variety of different orientations with opening 32 in different positions relative to the brief.

Alternatively, part 20 could be mounted on a piece of material separate from the brief. A relatively large portion of wall 12 of the brief could be cut away. The material upon which part 20 is mounted could then be position adjustably mounted on the brief, through the use of velco strips or the like. In this manner, the position of part 20 could be adjusted relative to the brief.

The internal diameters of each of the substantially rigid annular parts are substantially larger than the diameter of the penis such that the penis freely extends therethrough without being engaged or squeezed. The interior diameter of the receptacle A is substantially larger than the internal diameter of part 42 and, therefore, substantially larger than the diameter of the penis. In receptacle A', the walls of member 80 are highly elastic and loosely surround the penis without squeezing or exerting any substantial force thereon. Accordingly, the penis is freely received within receptacle A or A' in a non-load bearing manner.

If receptical A is used, the lower end of the receptacle is anchored to the leg of the patient. Urine from the penis will move downwardly within receptacle A and, thereafter, between the rear surface of baffle 50 and the interior surface of wall 41 and through aperture 56 of the non-return valve until it is situated at the bottom of the receptacle. When the receptacle is filled, plug 64 is removed from member 58 such that the receptacle may be emptied.

If receptacle A' is used, conduit 86 is connected between member 80 and bag 90 which may be attached to the patient's leg. Urine will flow from the penis, through member 80 and conduit 86 into bag 90. Bag 90 may be emptied through outlet port 96.

It should now be appreciated that in applicant's invention, the penis is not tightly engaged, nor is any significant force exerted thereon as it is freely received within the device. The entire weight of the receptacle and the urine therein is supported by the rreleasable interengaging annular parts and, thus, by the brief. The invention consists of several interconnectable parts which permit the device to be easily situated on the body of the user. Moreover, in one embodiment, the necessity for a discharge tube is eliminated such that no "kinking", resulting in urine back-up, can occur.

The male incontinence device of the present invention is composed of simple, inexpensive parts which can be manufactured utilizing standard techniques and which will cooperate together reliably.

While only a limited number of preferred embodiments of the present invention has been disclosed herein for purposes of illustration, it is obvious that many variations and modifications could be made thereto. It is intended to cover all of these modifications and variations which fall within the scope of the present invention, as defined by the following claims.

What we claim is:

1. A male incontinence device comprising an undergarment in the form of a brief, a flexible liquid collection receptacle, and means for releasably mounting said receptacle to said brief, said mounting means comprising first and second substantially rigid annular parts affixed to said brief and said receptacle, respectively, and means for releasably interengaging said first and second parts in a load bearing manner to support the weight of said receptacle, said brief comprising an opening adapted to be aligned with the penis, said brief opening being defined by said first part, said receptacle comprising an elongated, hollow member having an opening therein defined by said second part, said first and second parts having internal diameters substantially larger than the diameter of the penis to permit the penis to be freely received therethrough in a non-load-bearing manner, a flexible membrane adapted to be situated proximate said brief opening and having an expandable opening adapted to receive and lightly sealingly engage the penis, means for mounting said membrane to said brief, said means for mounting said membrane to said brief comprising a third substantially rigid annular part affixed to said brief, said first and third parts being mounted on opposite surfaces of said brief.

2. A male incontinence device comprising an undergarment in the form of a brief, a flexible liquid collection receptacle, and means for releasably mounting said receptacle to said brief, said mounting means comprising first and second substantially rigid annular parts affixed to said brief and said receptacle, respectively, and means for releasably interengaging said first and second parts in a load bearing manner to support the weight of said receptacle, said brief comprising an opening adapted to be aligned with the penis, said brief opening being defined by said first part, said receptacle comprising an elongated, hollow member having an opening therein defined by said second part, said first and second parts having internal diameters substantially larger than the diameter of the penis to permit the penis to be freely received therethrough in a non-load-bearing manner, a flexible membrane adapted to be situated proximate said brief opening and having an expandable opening adapted to receive and lightly sealingly engage the penis, means for mounting said membrane to said brief, said means for mounting said membrane to said brief comprising a third substantially rigid annular part affixed to said brief, said means for mounting said membrane further comprising a fourth substantially rigid annular part to which said membrane is mounted and means for releasably mounting said third and fourth parts.

3. A male incontinence device comprising an undergarment in the form of a brief, a flexible liquid collection receptacle, and means for releasably mounting said receptacle to said brief, said mounting means comprising first and second substantially rigid annular parts affixed to said brief and said receptacle, respectively, and means for releasably interengaging said first and second parts in a load bearing manner to support the weight of said receptacle, said brief comprising an opening adapted to be aligned with the penis, said brief opening being defined by said first part, said receptacle comprising an elongated, hollow member having an opening therein defined by said second part, said first and second parts having internal diameters substantially larger than the diameter of the penis to permit the penis to be freely received therethrough in a non-load-bearing manner, a flexible membrane adapted to be situated proximate said brief opening and having an expandable opening adapted to receive and lightly sealingly engage the penis, means for mounting said membrane to said brief, said means for mounting said membrane to said brief comprising a third substantially rigid annular part affixed to said brief, said membrane having a resilient end portion and wherein said resilient portion is adapted to engage said third part.

4. A male incontinence device comprising an undergarment in the form of a brief, a flexible liquid collection receptacle, and means for releasably mounting said receptacle to said brief, said mounting means comprising first and second substantially rigid annular parts affixed to said brief and said receptacle, respectively, and means for releasably interengaging said first and second parts in a load bearing manner to support the weight of said receptacle, said brief comprising an opening adapted to be aligned with the penis, said brief opening being defined by said first part, said receptacle comprising an elongated, hollow member having an opening therein defined by said second part, said first and second parts having internal diameters substantially larger than the diameter of the penis to permit the penis to be freely received therethrough in a non-load-bearing manner, a flexible membrane adapted to be situated proximate said brief opening and having an expandable opening adapted to receive and lightly sealingly engage the penis, means for mounting said membrane to said brief, said means for mounting said membrane to said brief comprising a third substantially rigid annular part affixed to said brief, said first part comprising an outwardly extending flange and further comprising means for affixing said flange to said brief, said third part comprising an outwardly extending flange, said outwardly extending flange of said third part being substantially aligned with said outwardly extending flange of said first part, said outwardly extending flange of said first part and said outwardly extending flange of said third part being spaced from each other to define a recess therebetween into which a portion of said brief is adapted to be received.

5. A male incontinence device comprising an undergarment in the form of a brief, a flexible liquid collection receptacle, and means for releasably mounting said receptacle to said brief, said mounting means comprising first and second substantially rigid annular parts affixed to said brief and said receptacle, respectively, and means for releasably interengaging said first and second parts in a load bearing manner to support the weight of said receptacle, said brief comprising an opening adapted to be aligned with the penis, said brief opening being defined by said first part, said receptacle comprising an elongated, hollow member having an opening therein defined by said second part, said first and second parts having internal diameters substantially larger than the diameter of the penis to permit the penis to be freely received therethrough in a non-load-bearing manner, a flexible membrane adapted to be situated proximate said brief opening and having an expandable opening adapted to receive and lightly sealingly engage the penis, means for mounting said membrane to said brief, said means for mounting said membrane to said brief comprising a third substantially rigid annular part affixed to said brief, wherein said third part comprises an annular protrusion and wherein said membrane comprises a ring-like end portion adapted to engage said annular protrusion.

6. A male incontinence device comprising an undergarment in the form of a brief, a flexible liquid collection receptacle, and means for releasably mounting said receptacle to said brief, said mounting means comprising first and second substantially rigid annular parts affixed to said brief and said receptacle, respectively, and means for releaably interengaging said first and second parts in a laod bearing manner to support the weight of said receptacle, said brief comprising an opening adapted to be aligned with the penis, said brief opening being defined by said first part, said receptacle comprising an elongated, hollow member having an opening therein defined by said second part, said first and second parts having internal diameters substantially larger than the diameter of the penis to permit the penis to be freely received therethrough in a non-load-bearing manner, a flexible membrane adapted to be situated proximate said brief opening and having an expandable opening adapted to receive and lightly sealingly engage the penis, means for mounting said membrane to said brief, said means for mounting said membrane to said brief comprising a third substantially rigid annular part affixed to said brief, and a fourth substantially rigid annular part to which said membrane is mounted.

7. The device of claims 1, 2, 3, 4, 5 or 6, wherein said third part is substantially aligned with said first part.

8. The device of claims 1, 2, 3, 4, 5 or 6, wherein said first and third parts are integral.

9. The device of claims 1, 2, 3, 4, 5 or 6, wherein said third part is affixed to said first part.

10. The device of claims 1, 2, 3, 4, 5 or 6, wherein said first part comprises an outwardly extending flange and further comprising means for affixing said flange to said brief.

11. The device of claims 1, 2, 3, 4, 5 or 6, wherein said first part comprises an outwardly extending flange and further comprising means for affixing said flange to said brief.

12. The device of claim 11, wherein said third part comprises an outwardly extending flange, said outwardly extending flange of said third part being substantially aligned with said outwardly extending flange of said first part.

13. The device of claim 5, wherein said annular protrusion comprises a cylindrical rib over which said ring-like portion of said membrane is received.

14. The device of claims 1, 2, 3, 4, 5 or 6, further comprising means for anchoring the lower end of said member to the leg.

15. The device of claims 1, 2, 3, 4, 5 or 6, further comprising a non-return valve situated in said member below said second part.

16. The device of claims 1, 2, 3, 4, 5 or 6, wherein said interengaging means comprises an annular groove on one of said first and second parts and an annular protrusion on the other of said first and second parts.

17. The device of claims 1, 2, 3, 4, 5 or 6, further comprising an outlet port proximate the lower end of said member.

18. The device of claims 1, 2, 3, 4, 5 or 6, wherein said receptacle has an internal diameter substantially larger than that of the penis to permit the penis to be freely received therein in a non-load bearing manner.

19. The device of claims 1, 2, 3, 4, 5 or 6, wherein said receptacle comprises a flexible condom shaped member.

20. The device of claim 19, wherein said receptacle further comprises a port in said member, a liquid collection reservoir, and a flexible conduit operably connecting said port and said reservoir.

21. The device of claim 20, further comprising means for mounting said reservoir to the calf.

* * * * *

UNITED STATES PATENT AND TRADEMARK OFFICE
CERTIFICATE OF CORRECTION

PATENT NO. : 4,673,401

DATED : June 16, 1987

INVENTOR(S) : Ole R. Jensen et al

It is certified that error appears in the above-identified patent and that said Letters Patent is hereby corrected as shown below:

On the title page Insert

--(73) Assignee: E.R. Squibb & Sons, Inc., Princeton, New Jersey --.

Signed and Sealed this

Eighth Day of December, 1987

Attest:

DONALD J. QUIGG

Attesting Officer

Commissioner of Patents and Trademarks